US008579960B2

(12) United States Patent  (10) Patent No.: US 8,579,960 B2
Kramer-Brown et al.  (45) Date of Patent: Nov. 12, 2013

(54) MANUFACTURE OF FINE-GRAINED MATERIAL FOR USE IN MEDICAL DEVICES

(75) Inventors: Pamela A. Kramer-Brown, San Jose, CA (US); John William Morris, Jr., Oakland, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/523,718

(22) Filed: Jun. 14, 2012

(65) Prior Publication Data

US 2012/0265291 A1  Oct. 18, 2012

Related U.S. Application Data

(63) Continuation of application No. 11/771,819, filed on Jun. 29, 2007, now Pat. No. 8,211,164, which is a continuation of application No. 10/032,659, filed on Oct. 25, 2001.

(51) Int. Cl.
*A61F 2/06* (2013.01)
(52) U.S. Cl.
USPC ........................................................ 623/1.15
(58) Field of Classification Search
USPC ............................................ 623/1.15; 606/76
See application file for complete search history.

(56) References Cited

U.S. PATENT DOCUMENTS

| | | |
|---|---|---|
| 3,723,193 A | 3/1973 | Reimann |
| 3,895,972 A | 7/1975 | Woodilla, Jr. et al. |
| 3,987,658 A | 10/1976 | Herold |
| 3,998,623 A | 12/1976 | Lampe et al. |
| 4,012,795 A | 3/1977 | Dorre et al. |
| 4,021,271 A | 5/1977 | Roberts |
| 4,502,896 A | 3/1985 | Duerig et al. |
| 4,522,783 A | 6/1985 | Menicucci |
| 4,770,725 A | 9/1988 | Simpson et al. |

(Continued)

FOREIGN PATENT DOCUMENTS

| | | |
|---|---|---|
| EP | 0947592 | 10/1999 |
| JP | 08-232061 | 9/1996 |

(Continued)

OTHER PUBLICATIONS

U.S. Appl. No. 11/771,889, Dec. 4, 2012, Notice of Allowance.

(Continued)

*Primary Examiner* — Julian W Woo
(74) *Attorney, Agent, or Firm* — Workman Nydegger; Jonathan D. Feuchtwang

(57) ABSTRACT

Medical devices are manufactured from fine grained materials, processed from of a variety of metals and alloys, such as stainless steel, cobalt-chromium and nickel-titanium alloys. A fine grained metal or alloy is formed from a specimen rapidly heated to its recrystallization temperature, and then subjected to high temperature, multi-axial deformation, for example, by heavy cross-forging or swaging. The deformed specimen may be cooled and reheated to a second recrystallization temperature. The metal or alloy in the specimen is then allowed to recrystallize, such that the grain size is controlled by quenching the specimen to room temperature. A desired medical device is then configured from the fine grained material. Decreasing the average grain size of a substrate material and increasing the number of grains across a thickness of a strut or similar component of the medical device increases the strength of the device and imparts other beneficial properties into the device.

17 Claims, 8 Drawing Sheets

(56) References Cited

U.S. PATENT DOCUMENTS

| | | | |
|---|---|---|---|
| 4,830,003 | A | 5/1989 | Wolff et al. |
| 4,919,177 | A | 4/1990 | Homma |
| 4,919,323 | A | 4/1990 | Mahoney et al. |
| 5,092,940 | A | 3/1992 | Kimura et al. |
| 5,171,379 | A | 12/1992 | Kumar et al. |
| 5,294,239 | A | 3/1994 | Zoltzer et al. |
| 5,358,578 | A | 10/1994 | Tischhauser |
| 5,415,704 | A | 5/1995 | Davidson |
| 5,569,295 | A | 10/1996 | Lam |
| 5,843,175 | A * | 12/1998 | Frantzen .................. 623/1.15 |
| 5,855,600 | A | 1/1999 | Alt |
| 5,869,195 | A | 2/1999 | Ramanarayanan et al. |
| 5,904,062 | A | 5/1999 | Semiatin et al. |
| 5,954,724 | A | 9/1999 | Davidson |
| 5,983,983 | A | 11/1999 | Whateley |
| 6,062,776 | A | 5/2000 | Sandman et al. |
| 6,129,997 | A | 10/2000 | Braun et al. |
| 6,200,671 | B1 | 3/2001 | Lindskog et al. |
| 6,200,685 | B1 | 3/2001 | Davidson |
| 6,399,215 | B1 | 6/2002 | Zhu et al. |
| 6,402,859 | B1 | 6/2002 | Ishii et al. |
| 6,432,133 | B1 | 8/2002 | Lau et al. |
| 6,508,832 | B1 | 1/2003 | Jalisi et al. |
| 6,520,923 | B1 | 2/2003 | Jalisi |
| 6,569,270 | B2 | 5/2003 | Segal |
| 6,596,102 | B2 | 7/2003 | Homma |
| 6,767,416 | B2 | 7/2004 | Ishibashi et al. |
| 6,780,261 | B2 | 8/2004 | Trozera |
| 6,827,734 | B2 | 12/2004 | Fariabi |
| 6,955,288 | B2 | 10/2005 | Barnes et al. |
| 7,335,314 | B2 | 2/2008 | Wu et al. |
| 2002/0007880 | A1 | 1/2002 | Segal et al. |
| 2003/0018381 | A1 | 1/2003 | Whitcher et al. |
| 2003/0028246 | A1 | 2/2003 | Palmaz et al. |
| 2003/0083731 | A1 | 5/2003 | Kramer et al. |
| 2007/0255387 | A1 | 11/2007 | Kramer et al. |
| 2008/0015683 | A1 | 1/2008 | Kramer-Brown et al. |

FOREIGN PATENT DOCUMENTS

| | | |
|---|---|---|
| WO | WO 98/17836 | 4/1998 |
| WO | WO 01/35865 | 5/2001 |
| WO | WO 01/72349 | 10/2001 |
| WO | WO 03/035130 | 5/2003 |

OTHER PUBLICATIONS

Donadille, C., Valle, R., Dervin, P., and Penelle, R., "Development of Texture and Microstructure During Cold-Rolling and Annealing of F.C.C. Alloys: Example of an Austenitic Stainless Steel," Acta. Metall., vol. 37, 1989, pp. 1547-1571.

Sandberg, A. and Sandstrom, R., "Static recrystallization and hot ductility of molybdenum-nitrogenalloyed austenitic stainless steels in association with two- and multistep deformation," Materials Science and Technology, vol. 2, Sep. 1986, pp. 926-937.

Stolyyarov, V.V., Zhu, Y.T., Lowe, T.C., Islamgaliev, R.K., and Valiev, R.Z., "A Two Step SPD Processing of Ultrafine-grained Titanium," NanoStructured Materials, vol. 11, No. 7, 1999, pp. 947-954.

Suzuki, T., and Takaki, S., "Superplasticity of Metastable Austenitic Stainless Steels With Ultra Fine Grains," The Third Pacific Rim International Conference on Advanced Materials and Processing, Abstract, pp. 1826-1830.

Venugopal, S., Mannan, S.L., and Prasad. Y.V.R.K., "Processing map for cold and hot working of stainless steel type AISI 304," Journal of Nuclear Materials 206, 1993, pp. 77-81.

Venugopal, S., Mannan, S.L., and Prasad. Y.V.R.K., "Processing map for hot working of stainless steel type AISI 316L," Materials Science and Technology, vol. 9, Oct. 1993, pp. 899-906.

Zhu, Y.T. and Lowe, T.C. "Observations and issues on mechanisms of grain refinement during ECAP process," Materials Science and Engineering A291, 2000, pp. 46-53.

U.S. Appl. No. 10/032,659, Feb. 18, 2004, Office Action.
U.S. Appl. No. 10/032,659, Jun. 29, 2004, Office Action.
U.S. Appl. No. 10/032,659, Dec. 9, 2004, Office Action.
U.S. Appl. No. 10/032,659, Jun. 1, 2005, Office Action.
U.S. Appl. No. 10/032,659, Nov. 25, 2005, Office Action.
U.S. Appl. No. 10/032,659, May 10, 2006, Office Action.
U.S. Appl. No. 10/032,659, Nov. 2, 2006, Office Action.
U.S. Appl. No. 10/032,659, Jul. 9, 2007, Office Action.
U.S. Appl. No. 10/032,659, Jan. 3, 2008, Office Action.
U.S. Appl. No. 10/032,659, Aug. 13, 2008, Office Action.
U.S. Appl. No. 11/771,819, Sep. 22, 2010, Office Action.
U.S. Appl. No. 11/771,819, Dec. 22, 2010, Office Action.
U.S. Appl. No. 11/771,819, Jun. 29, 2011, Office Action.
U.S. Appl. No. 11/771,819, Jan. 10, 2012, Notice of Allowance.
U.S. Appl. No. 11/771,819, Apr. 11, 2012, Notice of Allowance.
U.S. Appl. No. 11/771,889, Sep. 22, 2010, Restriction Requirement.
U.S. Appl. No. 11/771,889, Nov. 17, 2010, Office Action.
U.S. Appl. No. 11/771,889, Apr. 28, 2011, Office Action.
U.S. Appl. No. 11/771,889, Sep. 1, 2011, Office Action.
U.S. Appl. No. 11/771,889, Feb. 2, 2012, Office Action.
U.S. Appl. No. 11/771,889, Aug. 3, 2012, Office Action.
U.S. Appl. No. 10/032,659, May 20, 2013, Notice of Allowance.

* cited by examiner

50 μm 0.3 μm

1 μm

1 μm

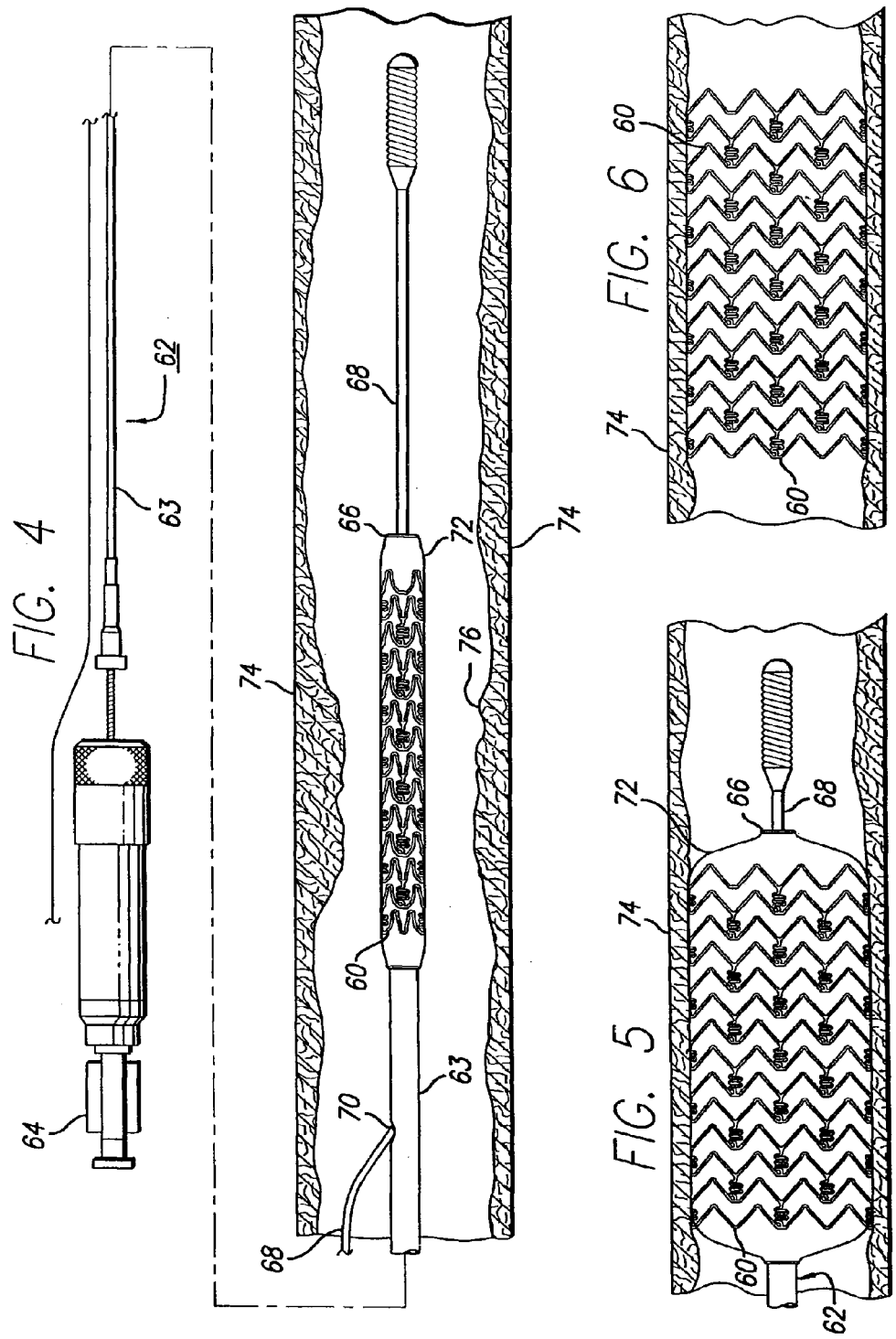

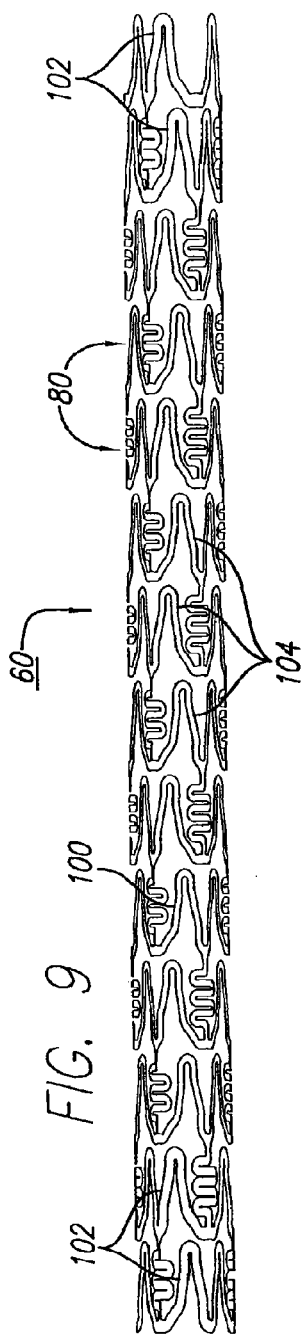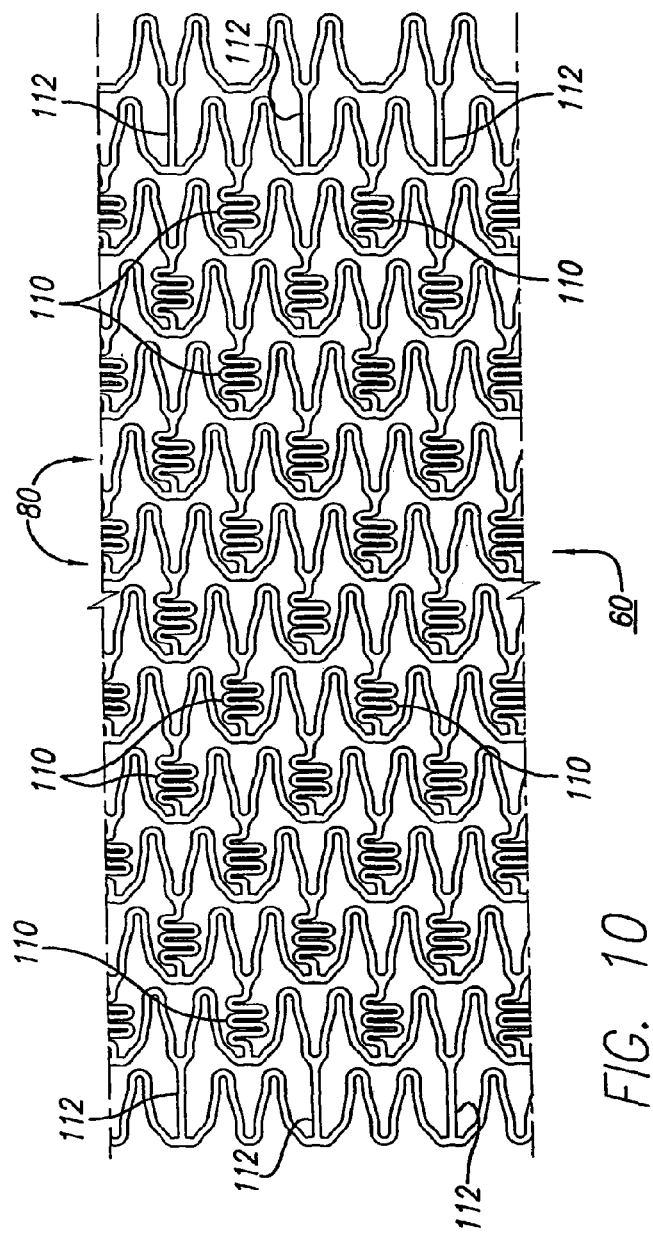
FIG. 9
FIG. 10

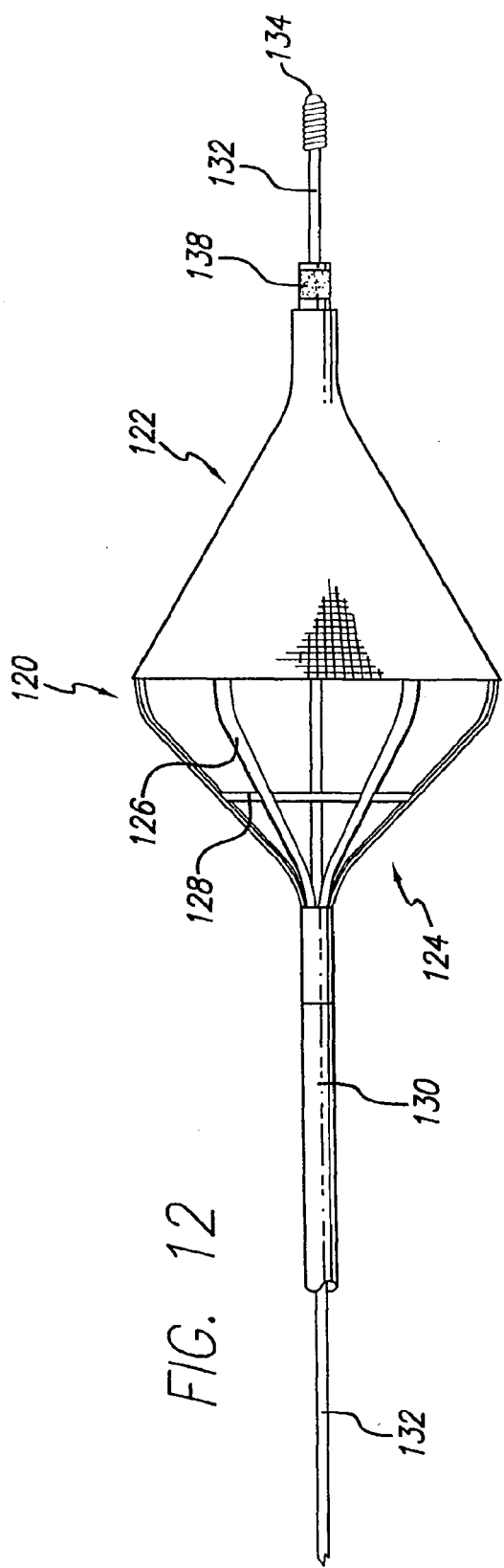
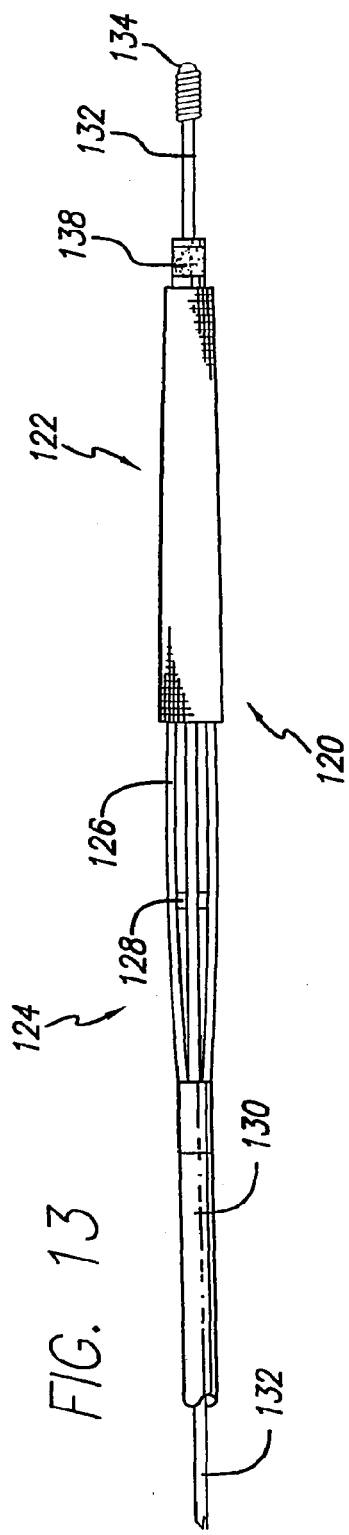
FIG. 12
FIG. 13

MANUFACTURE OF FINE-GRAINED MATERIAL FOR USE IN MEDICAL DEVICES

BACKGROUND OF THE INVENTION

This invention relates to medical devices, and more particularly to methods of manufacturing medical devices using fine grained metals and alloys.

A focus of recent development work in the treatment of heart disease has been directed to endoprosthetic devices referred to as stents. Stents are generally tubular shaped devices which function to maintain patency of a segment of a blood vessel or other body lumen such as a coronary artery. They also are suitable for use to support and hold back a dissected arterial lining that can occlude the fluid passageway. At present, there are numerous commercial stents being marketed throughout the world. Intraluminal stents implanted via percutaneous methods have become a standard adjunct to balloon angioplasty in the treatment of atherosclerotic disease. Stents prevent acute vessel recoil and improve the long term outcome by controlling negative remodeling and pinning vessel dissections. Amongst their many properties, stents must have adequate mechanical strength, flexibility, minimal recoil, and occupy the least amount of arterial surface area possible while not having large regions of unsupported area.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway thereof.

Stents are typically formed from biocompatible metals and alloys, such as stainless steel, nickel-titanium, platinum-iridium alloys, cobalt-chromium alloys and tantalum. Such stents provide sufficient hoop strength to perform the scaffolding function. Furthermore, stents should have minimal wall thicknesses in order to minimize blood flow blockage. However, stents can sometimes cause complications, including thrombosis and neointimal hyperplasia, such as by inducement of smooth muscle cell proliferation at the site of implantation of the stent. Starting stock for manufacturing stents is frequently in the form of stainless steel tubing.

The structural properties of the material used for implantable medical devices can improve with a decrease in the grain size of the substrate material. It has been observed that stents cut from fully annealed 316L stainless steel tubing having less than seven grains across a strut thickness can display micro cracks in the high strain regions of the stent. Such cracks are suggestive of heavy slip band formation, with subsequent decohesion along the slip planes. Reduction of the grain size in the substrate material, such as stainless steel, will reduce or eliminate the occurrence of such cracks and/or heavy slip band formation in the finished medical device.

The grain size of a finished stainless steel or similar metal tube depends on numerous factors, including the length of time the material is heated above a temperature that allows significant grain growth. For a metallic tube, if the grain size is larger than desired, the tube may be swaged to introduce heavy dislocation densities, then heat treated to recrystallize the material into finer grains. Alternatively, different material forms may be taken through a drawing or other working and heat treat processes to recrystallize the tubing. The type and amount of working allowed depends on the material, e.g., ceramics may require a high temperature working step while metals and composites may be workable at room temperature. Grain-size strengthening is where there is an increase in strength of a material due to a decrease in the grain size. The larger grain-boundary area more effectively blocks dislocation movement. The outer diameter of the tube usually requires a machining step of some sort to smooth the surface after the swaging process, and the same may be true before the tubing can be properly drawn.

Commercially available 316L stainless steel tubing contains average grain sizes ranging from approximately 0.0025 inch (sixty four microns), ASTM grain size 5 to around 0.00088 inch (twenty two microns), ASTM grain size 8. These grain sizes result in anywhere from two to five grains across the tube thickness, and the stent subsequently manufactured from the tubing, depending on the tube and stent strut thicknesses. Part of the limitation in achieving a finer grain size in this material arises from the number of draws and anneals the tubing must go through to achieve its final size. The potential for reducing the grain size exists by reducing the required number of heat-processing steps by reducing the starting size of the raw product that is then processed down into the tubing.

Lowering the grain size and increasing the number of grains across the strut thickness of a stent allows the grains within the stent to act more as a continuum and less as a step function. The ideal result of processing the material to a smaller grain size would result in an average grain size of between approximately one and ten microns, with a subsequent average number of grains across the strut thickness about seven or greater. Likewise, other medical devices will benefit from a reduction in grain size such as guide wires, ring markers, defibrillator lead tips, delivery system devices such as catheters, and the like.

What has been needed, and heretofore unavailable, in the art of medical device design is fine grained metals and alloys that have uniform and predictable properties and that contain grain sizes on the order of one to ten microns. The present invention satisfies these and other needs.

SUMMARY OF THE INVENTION

Briefly, and in general terms, the present invention is directed to the manufacture and use of fine grained (less than twenty microns in diameter) metals and alloys for use in medical devices. Medical devices configured from fine grained material have many uses, including, but not limited to, incorporation into stents, embolic protection devices, graft attachment systems, guide wires, pacing leads for cardiac pacemakers, defibrillator lead tips, ring markers, catheters, delivery systems, anastomosis clips and other tube or wire implants. The present invention for manufacture and use of fine grained materials may be applied to the processing of a variety of metals and alloys, such as stainless steel and nitinol. Decreasing the average grain size of a substrate material and increasing the number of grains across a thickness of a strut or similar component of the medical device may increase the strength and ductility of the device or impart other beneficial properties into the device.

The present invention includes methods of manufacturing fine grained materials for use in medical devices. Similarly, the present invention includes medical devices made from such fine grained materials. The novelty of the fine grained manufacturing process includes subjecting a specimen of a metal or metal alloy to multi-axial deformation (for example, by heavy cross-forging or swaging) at elevated temperatures within the recrystallization regime of the specimen. The specimen is then cooled to about room temperature to halt the recrystallization process, so as to achieve the desired grain size in the specimen.

A variety of manufacturing methods may be employed to manufacture medical devices of the present invention from a fine grained material. Such medical devices may be formed from a tube made from a fine grained material by laser cutting the pattern of the device in the tube. The medical device also may be formed by laser cutting a flat fine grained metal (alloy) sheet in the pattern of the device, rolling the sheet into a tubular shape and then providing a longitudinal weld to form the device, such as a stent. In addition, such a device may be formed from a wire or elongated fiber constructed from fine grained material. Stents and other implantable devices formed from such fine grained materials may be used with conventional over the wire or rapid exchange delivery systems, and deployed into a patient's vasculature in a conventional manner.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 4 is an elevational view, partially in section, of a fine grain stent embodying features of the invention, wherein the stent is mounted on a rapid-exchange delivery catheter and a fine grain guide wire.

FIG. 5 is an elevational view, partially in section, of a fine grain stent embodying features of the invention, wherein the stent is expanded within an artery, so that the stent apposes an arterial wall.

FIG. 6 is an elevational view, partially in section, of an expanded fine grain stent embodying features of the invention, wherein the stent is implanted within an artery after withdrawal of a delivery catheter.

FIG. 9 is a side view of a fine grain stent embodying features of the invention, depicting cylindrical rings at the end of the stent having a thicker cross section than the rings at the center of the stent.

FIG. 10 is a plan view of a flattened fine grain stent embodying features of the invention, illustrating a combination of undulating links and straight links.

FIG. 12 depicts a longitudinal plan view of an embodiment of an expanded embolic protection device, including fine grain expandable struts of the present invention.

FIG. 13 depicts a longitudinal plan view of the embolic protection device of FIG. 12, wherein the device is collapsed for delivery into a corporal lumen.

DETAILED DESCRIPTION OF THE PREFERRED EMBODIMENTS

Figure 1:
FIG. 1 is an optical micrograph of annealed 316L stainless steel.

As shown in the drawings for purposes of illustration, the present invention is directed to the manufacture and use of fine grained metals and alloys for forming material such as tube stock, a piece of tubing, a wire and the like for use in intravascular and other medical devices. The novelty of the fine grained manufacturing process of the present invention includes subjecting a specimen of a metal or metal alloy to multi axial deformation (for example, by heavy cross forging or swaging) at elevated temperatures within the recrystallization regime of the specimen. The specimen is then cooled to about room temperature to halt the recrystallization process, so as to achieve the desired grain size in the specimen.

The fine grained material manufactured by the process of the present invention has many uses, including, but not limited to, incorporation into medical devices, such as a stents, embolic protection devices, graft attachment systems, guide wires, pacing leads for cardiac pacemakers, defibrillator lead tips, ring markers, catheters, delivery systems, anastomosis clips and other tube or wire implants. The present invention for manufacture of fine grained hypotube and wire may be applied to many material types, including, but not limited to, processing of 316L stainless steel, cobalt-chromium alloys, nickel-titanium alloys, platinum-iridium alloys, titanium and titanium based alloys, tantalum and tantalum based alloys, and other suitable alloy systems. While virtually any medical device that is implanted or used in the body will benefit from the present invention, the invention as applied to stents is described herein as only an example and is not meant to be limiting.

One embodiment of the present invention is the grain refinement of 316L, an austenitic stainless steel that is widely used in medical devices (FIG. 1). One motivation for such grain refinement is to produce a material that will have uniform and predictable properties in sizes that may be less than one hundred microns in various dimensions, which can be on the order of the grain size in annealed material. Current 316L stainless steel hypotube used in manufacturing medical device products can have average grain sizes ranging from approximately 0.0025 inches (sixty four microns), ASTM grain size 5, to around 0.00088 inches (twenty two microns), ASTM grain size 8. These grain sizes result in an average of two to five grains across the wall thickness of the hypotube, and result in a similar number of grains across the width or thickness of a stent strut manufactured from the hypotube. Lowering the grain size and increasing the number of grains across the strut thickness allows the grains within the stent to act more as a continuum and less as a step function, thereby providing a better distribution of the stresses within the grains to other grains, so as to increase the strength and ductility of the fine grained material.

The ideal result of processing 316L stainless steel for use in a medical device to a smaller grain size would result in an average grain size of less than twenty microns ("fine grained"). With respect to medical devices that incorporate 316L stainless steel struts, shafts, links and similar elongated elements (such as stents and graft attachment systems) having a thickness of about one hundred microns, such elements should have an average of about seven or more grains across the thickness of the element (preferably five to twenty grains across). Similarly, for such devices having a strut thickness of about fifty microns (such as portions of embolic protection devices), such elements should have an average of about three or more grains across the thickness of the element (preferably two to fifteen grains across). Likewise, for medical devices incorporating 316L stainless steel wires or wire like elements (such as guide wires, pacing leads and defribillator leads) having a diameter of about three hundred and fifty microns, the wire should have an average of about thirty or more grains across the thickness of the element (preferably twenty to sixty grains across). Similar calculations may be readily made by one of ordinary skill in the art for varying dimensions of the device, and for different metals and metal alloys.

There are four generic ways to produce a fine grained material: recrystallization, martensite reversion, powder consolidation and metal injection molding. The present invention is directed to recrystallization of metals and alloys, for example, 316L stainless steel. If a material is severely deformed and then heated to a sufficiently high temperature the microstructural damage caused by the deformation is relieved by the nucleation of new, nominally defect-free grains which grow together to consume the deformed material. This process is known as "recrystallization," which occurs above a temperature, the "recrystallization temperature," whose value depends on the extent of prior deformation. In the example case of 316L stainless steel, that temperature is several hundred degrees centigrade (° C.).

The grain boundaries and local damage sites in the deformed material provide the preferential sites for nucleation of the recrystallized grains. If the material is severely deformed the density of such sites is very high and recrystallization begins with a dense shower of nuclei. The growing nuclei impinge on one another very quickly during growth to form a fine grained product. The fine grain size can be preserved by quenching the material to low temperature to prevent further grain growth.

There are two basic ways to use recrystallization to obtain fine grain size, as is well known to one of ordinary skill in the art. The simplest is to impose a severe deformation at high temperature, above the recrystallization temperature, so that recrystallization occurs almost immediately after deformation, then quench the material rapidly to room temperature. The most obviously attractive method of high temperature deformation is hot forging at high strain rate, though other methods, such as rapid rolling or swaging, can also be used. In current practice, high-temperature, high-rate forging has been used to achieve one micron grain size in ferritic steel. Prior to the present invention, the applicability of such recrystallization to 316L austenitic stainless steel for use in medical devices had not yet been demonstrated.

The second method to use recrystallization to obtain fine grain size is to deform the steel while it is cold, for example, by cold drawing, swaging or hydrostatic extrusion, and recrystallize by subsequent heating. This method offers a possible advantage in that it may be more compatible with near-net shape forming operations to manufacture suitable tubes. However, it is likely to be more difficult to use for grain refinement, since it requires close control over the heating cycle used to accomplish the recrystallization.

There are two generic ways to form material into small diameter, thin walled tubes (hypotube) and wire. The material may be created with fine grains then formed after the fact, or the material may be formed into a fine grain using near-net shape processes where the hypotube or wire formation is part of the operation that refines the grain size. Drawing a material created with fine grains into seamless hypotube may be challenging, since grain refinement increases the strength of the material via the Hall-Petch effect. However, two methods of forming a material created with fine grains into seamless hypotube are currently available.

In the first method, the material may be grain refined then formed into a small diameter rod or wire by shape rolling, swaging or hydrostatic extrusion. The wire may then be gun drilled and machined into a tube of suitable dimensions. Alternatively, the grain refined material may be drawn into a relatively large diameter tube, filled with a substance that is easily deformed, such as aluminum or copper, then wire drawn or hydrostatically extruded into a small diameter wire. Afterwards the filler material may be melted, etched or dissolved out and the tubing finished to final specifications.

The second method of forming processes includes near-net shape techniques that form the tube either before or concomitantly with grain refinement. When recrystallization is used to accomplish the grain refinement, then the deformation that drives recrystallization can be used to form a wire or hypotube through wire drawing, tube drawing, rolling or extrusion techniques. If the deformation is per formed at high temperatures, recrystallization will accompany it. If the deformation is performed at low temperature, recrystallization can be accomplished by heating the material after the deformation operation. In either case, there is the potential of recrystallization producing some geometric distortion which may then be corrected using finishing operations to achieve the specified dimensions and shape.

The extent of recrystallization on hot deformation is the result of a competition between two processes. The first is plastic deformation, which deforms the grains and introduces the excess energy that is the driving force for recrystallization. To achieve uniform recrystallization, the deformation must not only be extensive, but also reasonably homogeneous, so that all grains are deformed, and stable against recovery for a long enough time to nucleate recrystallization, so that the driving force is preserved. The second process is temperature based. As the temperature becomes very high, plastic deformation becomes ineffective. The microstructure softens with the consequence that deformation becomes inhomogeneous, leaving relatively undeformed islands in the micro structure, and recovery becomes rapid and competes with recrystallization as a mechanism for relieving the strain. A grain size of about three to six microns is close to the optimal size for use in medical devices, since the grains are small enough to ensure polygranular behavior in thin sections while keeping the strength low enough for reasonable formability.

By way of example, the recrystallization method of the present invention may be used on annealed or cold worked specimens of starting material, such as 316L stainless steel. The annealed and cold-worked specimens yield similar microstructures in the as forged condition, since the hot deformation overwhelms any prior deformation. Moreover, the hardness of the specimens is not changed dramatically by the forging process of the present invention. The hardness of the annealed specimens may increase slightly, while that of the cold worked specimens may decrease slightly. In both cases, the as-forged hardness for 316L stainless steel upon completion of the recrystallization of the present invention is expected to be about 29 Rc.

The recrystallization process of the present invention includes high temperature multi axial deformation (for example, by heavy forging or cross-forging), which may be in the range of seventy five to ninety five percent net deformation of the target specimen. To aid in the forging process, a suitable forging machine may be used, such as the one constructed at the National Research Institute for Metals in Tsukuba, Japan (NRIM). The Japanese NRIM forging machine contains two opposed TiC (titanium carbide) anvils, both of which move into the specimen in the form of a 15×15×100 mm metal bar. Other sized bars or metal billets may be used, depending on the forging apparatus used. The NRIM machine forges at a set strain rate, which is achieved by controlling the final displacement of the anvils. The two anvils are moved equally toward one another, so that the neutral axis remains at the centerline of the specimen, and so that there is no macroscopic bending of the specimen. The specimen may be first forged to a selected displacement, and then rotated ninety degrees and forged to a second set displacement. For example, the specimen may be first forged to a displacement of fifty percent, rotated and then forged to a displacement of fifty percent, yielding a net deformation of eighty percent.

A suitable multi-axial forging or swaging apparatus should have the capability of either static or continuous multi axial forging or swaging. Such a machine should have the capability to deform a target specimen in more than one orthogonal direction. For example, the multi-axial deformation may be performed in thirty, sixty or ninety degree increments. The range of deformation may surround the specimen (360°), or other suitable increments, such as two ninety degree deformations. An example of a static multi axial forging machine exists at NRIM.

In addition, a suitable multi axial forging or swaging machine should also include the capability to heat the specimen to a variety of temperatures at various heating rates, or should be able to accept a specimen pre-heated at the appropriate rate from another machine prior to insertion in the forging or swaging machine. Those of ordinary skill in the art of metallurgy will recognize that the rate of heating the specimen to the recrystallization temperature should avoid recovery (for example, at about ten ° C. per second or less). Likewise, it should be recognized that while faster heating rates may be employed, care should be taken to avoid distorting the shape and configuration of the specimen.

In addition, such an apparatus should be capable of drawing a vacuum around the specimen or maintaining an atmosphere of inert gas or other gas compatible with the specimen, so as to prevent oxidation of the metal during the forging or swaging process. Further, the apparatus or a closely situated other apparatus should allow the capability to quickly reduce the temperature of the specimen by any suitable means to control and halt the growth of the metal grain size, for example, by air cooling, or by quenching with water, oil or liquid nitrogen. The machine should have the capability of either static or continuous multi-axial forging or swaging.

Fine-grained stainless steel may be formed using the recrystallization process of the present invention. In accordance with the inventive process, a 316L stainless steel cold-worked or annealed specimen is placed in a forging machine or similar apparatus. Air is then evacuated from the forging machine, and an inert gas or other gas compatible with the specimen to prevent oxidation may be introduced. The stainless steel specimen is then heated to a desired temperature in the range of about 800 to 1100° C. The temperature of the specimen in the machine is then stabilized.

In one embodiment of the recrystallization process of the present invention, the 316L stainless steel specimen is forged or heavily deformed in multiple passes at the stabilized temperature to a high net deformation, for example, eighty percent. The specimen is then held at the stabilized temperature for one to ten minutes to allow recrystallization, and then quenched to about room temperature to fix the grain size. The expected resulting grain size of the fine grained material from this process is one to ten microns (less than eleven microns).

In another embodiment of the recrystallization process of the present invention, the 316L stainless steel specimen is heavily forged at the stabilized temperature, for example, using fifty percent plus fifty percent cross forging to yield eighty percent net deformation. After forging, the specimen is then cooled to about room temperature in water, or by other suitable means. The stainless steel specimen is then heated at a moderate rate (for purposes of illustration, at about ten ° C. per second) to avoid too much recovery before reaching the recrystallization temperature in the range of 800 to 900° C. The specimen is held at that temperature for one to ten minutes to control the grain size, and then the specimen is quenched to about room temperature to halt recrystallization. The expected resulting grain size of the fine grained material from this process is one to ten microns (less than eleven microns).

Further embodiments of the process of the present invention may be used to form fine grained materials using other metals and alloys, by varying the recrystallization temperature and time to achieve the desired grain size. This elevated temperature, multi axial deformation process applies to a wide range of metals and alloys, which may employ heat treatment schedules commonly utilized for annealing or recrystallization purposes. Such heat treatment schedules are well known to those of ordinary skill in the art. Example alloys for which the fine grained manufacturing method of the present invention may be applied include, but are not limited to:

1. L 605 (ASTM F90 and AMS 5759), a Co—Cr—W—Ni alloy also available as STELLITE 25 (Deloro Stellite Company, Inc., South Bend, Ind., U.S.A.) and HAYNES 25 (Haynes International Inc., Kokomo, Ind., U.S.A.), which should be heated to a recrystallization temperature ranging between 1120 and 1230° C., and must have rapid cooling (e.g., air) in order to avoid precipitation of undesirable phases;
2. ELGILOY (ASTM F1058), a Co—Cr—Mo—Ni alloy available from Elgiloy Specialty Metals Division of Elgin, Ill., U.S.A., which should be heated to a recrystallization temperature ranging from 1090 to 1150° C.;
3. Platinum iridium (Pt Ir) alloys, which should be heated to a recrystallization temperature ranging from 1000 to 1200° C. for alloys having up to ten percent iridium, and ranging from 1300 to 1500° C. for alloys having greater than ten percent iridium;
4. Nickel-titanium (Ni Ti) alloys (e.g., nitinol having stoichiometry around 50-50 for shape memory properties), which should be heated to a recrystallization temperature ranging from 650 to 950° C., with longer hold times for the lower temperatures;
5. Tantalum (Ta) and tantalum based alloys, such that pure tantalum is heated to a recrystallization temperature ranging from 1260 to 1370° C., with temperatures for tantalum alloys depending on the particular alloy; and
6. Titanium (Ti) and titanium based alloys, such that pure titanium is heated to a recrystallization temperature ranging from 650 to 750° C., with temperatures for titanium alloys depending on the particular alloy.

Example 1

Figure 2:
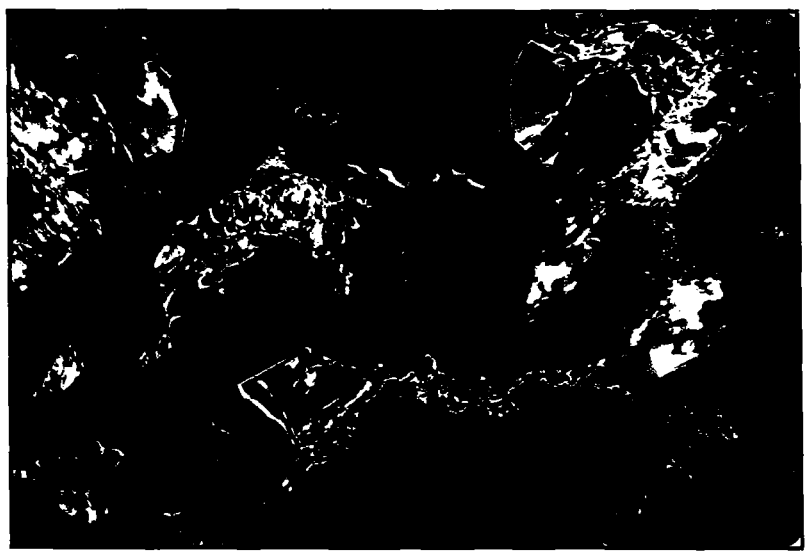
FIG. 2 is a transmission electron micrograph of fine grain stainless steel embodying features of the present invention.

A 316L stainless steel specimen in the form of a rectangular bar, 15×15×100 mm in size, is placed into a forging machine, such as the one heretofore described at the Japanese NRIM. Air is then evacuated from the forging machine, and the stainless steel specimen is heated to 800° C. at a rate of about ten ° C./sec. The specimen is held in the machine at 800° C. for one minute to stabilize the specimen temperature, and then forged immediately. The specimen is subjected cross-forging to a net deformation of eighty percent. The specimen is then held at 800° C. for up to five minutes to control the grain size to the desired level of about five microns. The specimen may then be air cooled or water quenched to room temperature to halt the recrystallization process. FIG. 2 depicts a transmission electron micrograph of a typical section of a 316L stainless steel specimen resulting from this process.

Example 2

Figure 3A:
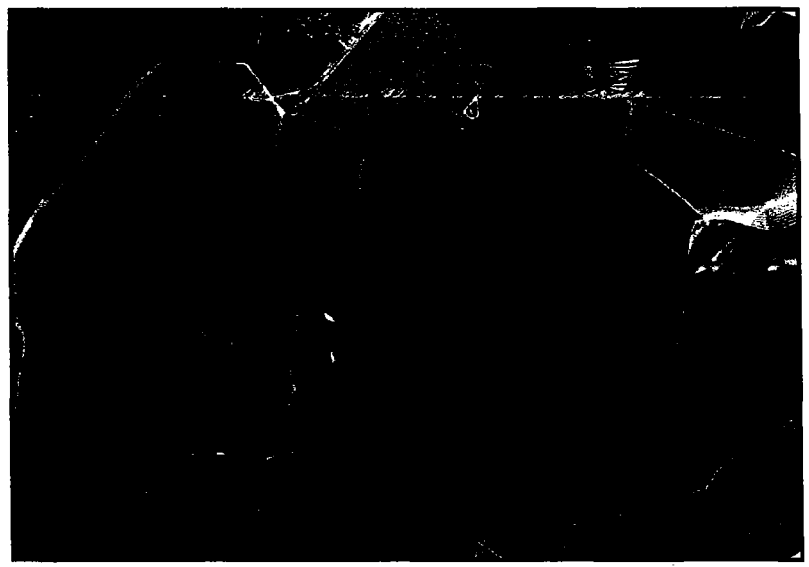
FIGS. 3A and 3B are transmission electron micrographs of fine grain stainless steel embodying features of the present invention.
Figure 3B:
Figure 7:
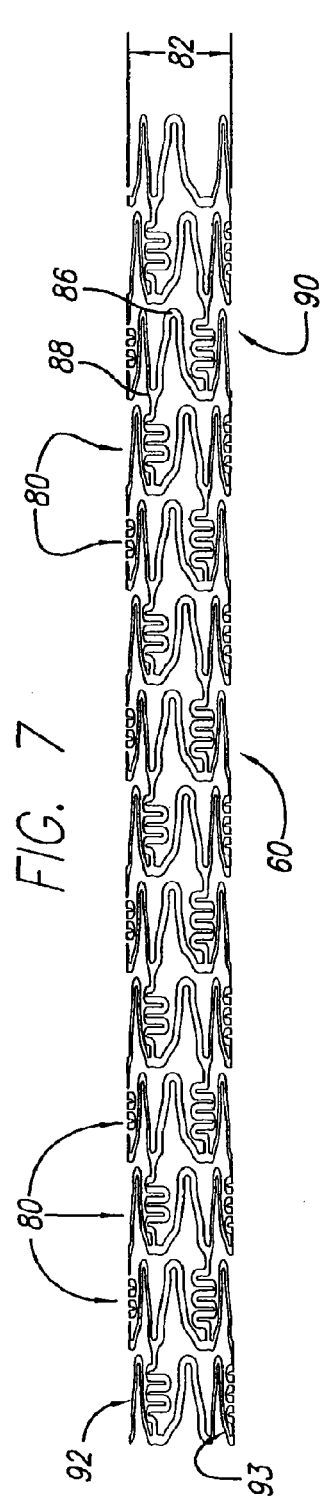
FIG. 7 is a side view of a fine grain stent embodying features of the invention, wherein the stent is in an unexpanded state.

A 316L stainless steel specimen in the form of a rectangular bar, 15×15×100 mm in size, is placed in a forging machine, such as the one heretofore described at the Japanese NRIM. Air is then evacuated from the forging machine. The stainless steel specimen is then heated to 800° C. at a rate of about ten ° C./sec. The specimen is held for in the machine at 800° C. for one minute to stabilize the specimen temperature, and then forged immediately. The specimen is then subjected to cross-forging to a net deformation of eighty percent. The specimen is then cooled to room temperature in water. The specimen is subsequently heated to 900° C. at a rate of about ten ° C./sec and held at that temperature for two minutes, and then air cooled or water quenched to room temperature to halt recrystallization. FIGS. 3A and 3B depict transmission electron micrographs of typical sections of a 316L stainless steel specimen resulting from this process.

Stents are well known in the art and can have many different types of patterns and configurations. The following description of intravascular stents, as shown in FIGS. 4-11, are typical stent patterns made from stainless steel tubing. Other patterns are well known in the art, and the description herein of stents and delivery systems is by way of example and is not meant to be limiting.

Referring to FIG. 4, a stent 60 constructed from a fine grain material, such as 316L stainless steel, may be mounted on a catheter assembly 62, which is used to deliver the stent and implant it in a body lumen, such as a coronary artery, peripheral artery, or other vessel or lumen within the body. The catheter assembly includes a catheter shaft 63, which has a proximal end 64 and a distal end 66. The catheter assembly is configured to advance through the patient's vascular system by advancing over a guide wire 68 by any of the well known methods utilizing an over the wire system (not shown), or a rapid exchange (RX) catheter system, such as the one shown in FIG. 4. The guide wire may also be constructed from a fine grain material according to the processes of the present invention Catheter assembly 62, as depicted in FIG. 4, is of the well known rapid exchange type that includes an RX port 70, where the guide wire 68 will exit the catheter shaft 63. The distal end of the guide wire exits the catheter distal end 66 so that the catheter advances along the guide wire on a section of the catheter between the RX port and the catheter distal end. As is known in the art, a guide wire lumen (not shown) is configured and sized for receiving various diameter guide wires to suit a particular application.

The fine grain stent 60 is typically mounted on an expandable member (balloon) 72 positioned proximate the catheter distal end 66. The stent is crimped tightly thereon, so that the stent and expandable member present a low profile diameter for delivery through the patient's vasculature. The stent may be used to repair a diseased or damaged arterial wall 74, which may include plaque 76, a dissection or a flap that are commonly found in the coronary arteries, peripheral arteries and other vessels. Such plaque may be treated by an angioplasty or other repair procedure prior to stent implantation.

In a typical procedure to implant a stent 60 formed from a fine grain material, the guide wire 68 is advanced through the patient's vascular system by well known methods so that the distal end of the guide wire is advanced past the plaque or diseased area 76. Prior to implanting the stent, the cardiologist may wish to perform an angioplasty procedure or other procedure (e.g., atherectomy) in order to open the vessel and remodel the diseased area. Thereafter, the stent delivery catheter assembly 62 is advanced over the guide wire so that the stent is positioned in the target area. During positioning and throughout the procedure, the fine grain stent may be visualized through x ray fluoroscopy and/or magnetic resonance angiography.

As shown in FIG. 5, the expandable member or balloon 72 is inflated by well known means so that it expands radially outwardly and in turn expands the fine grain stent 60 radially outwardly until the stent is apposed to the vessel wall 74. The balloon is fully inflated with the stent expanded and pressed against the vessel wall. The expandable member is then deflated, and the catheter assembly 62 is withdrawn from the patient's vascular system. The guide wire 68 typically is left in the vessel for post dilatation procedures, if any, and subsequently is withdrawn from the patient's vascular system. As depicted in FIG. 6, the implanted stent remains in the vessel after the balloon has been deflated and the catheter assembly and guide wire have been withdrawn from the patient.

The stent 60 formed from a fine grain material serves to hold open the artery wall 74 after the catheter assembly 62 is withdrawn, as illustrated by FIG. 6. Due to the formation of the stent from an elongated tubular member, the undulating components of the stent are relatively flat in transverse cross section, so that when the stent is expanded, it is pressed into the wall of the artery and as a result does not interfere with the blood flow through the artery. The stent is pressed into the wall of the artery and will eventually be covered with endothelial cell growth, which further minimizes blood flow interference. The undulating ring portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 5 and 6.

Figure 8:
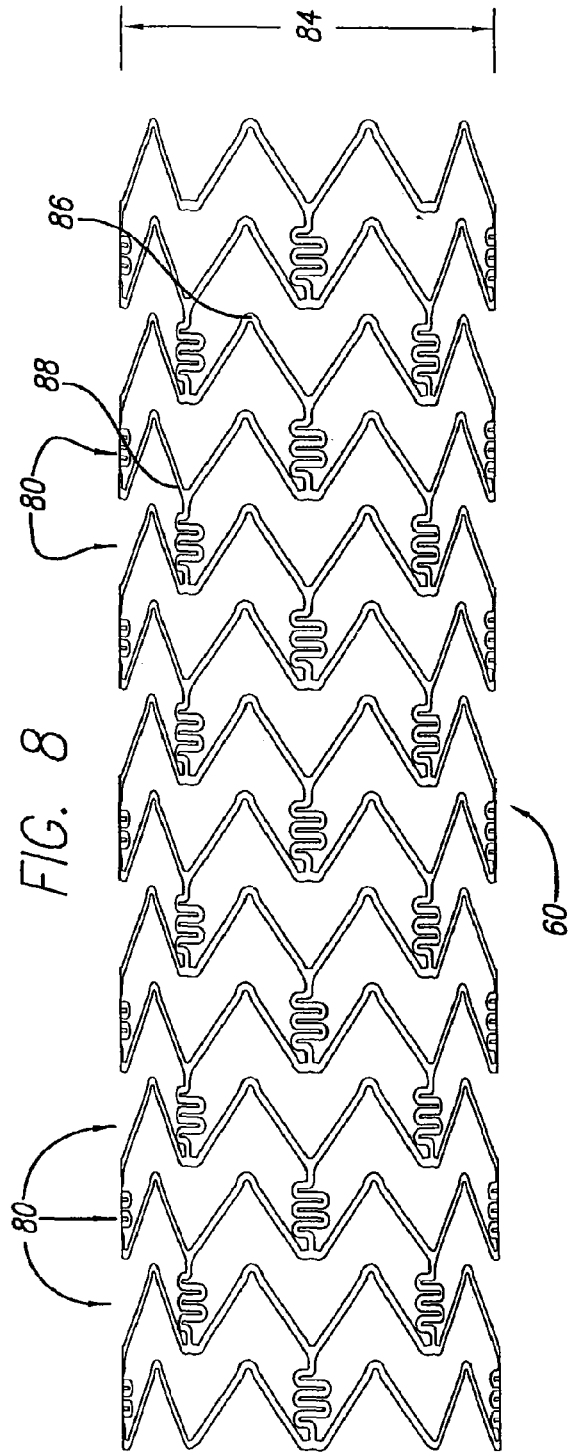
FIG. 8 is a side view of the fine grain stent of FIG. 7 in an expanded condition, depicting cylindrical rings connected by undulating links.

As shown in FIGS. 7-11, the fine grain stent 60 is made up of a plurality of cylindrical rings 80, which extend circumferentially around the stent. The stent has a delivery diameter 82 (FIG. 7), and an implanted diameter 84 (FIG. 8). Each cylindrical ring 80 has a proximal end 86 and a distal end 88. When the stent is laser cut from a solid tube, there are no discreet parts, such as the described cylindrical rings. However, it is beneficial for identification and reference to various parts to refer to the cylindrical rings and the following parts of the stent.

Each cylindrical ring 80 defines a cylindrical plane 90, which is bound by the cylindrical ring proximal end 86, the cylindrical ring distal end 88 and the circumferential extent as the cylindrical ring 80 traverses around the cylinder. Each cylindrical ring includes a cylindrical outer wall surface 92, which defines the outer most surface of the fine grain stent 60, and a cylindrical inner wall surface 93, which defines the innermost surface of the stent. The cylindrical plane follows the cylindrical outer wall surface.

As shown in FIGS. 9 and 10, the stent 60 may be constructed with struts 100 formed from fine grain material having a variable thickness along the stent length. As one example, it is contemplated that struts 102 at the ends of the stent may be thicker than the struts 104 in the center of the stent for purposes for increased radiopacity and to counter non-uniform balloon expansion. When the balloon first inflates, the balloon ends have a tendency to inflate at a faster rate than the balloon center. However, with thicker struts at the stent ends, the balloon, and hence the stent, will expand more uniformly.

Figure 11:
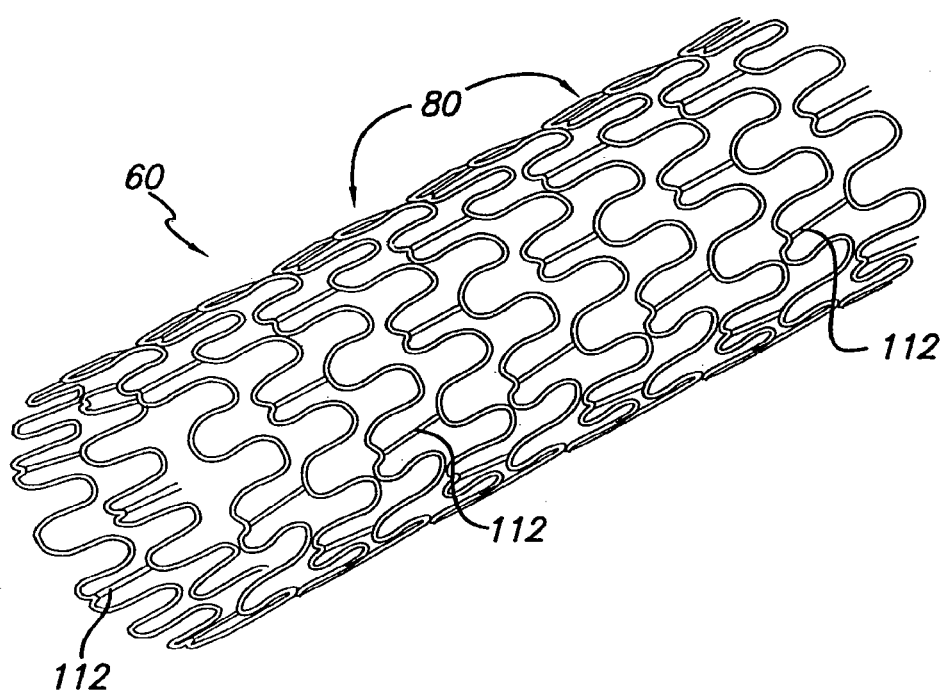
FIG. 11 is a perspective view of a fine grain stent embodying features of the invention, depicting cylindrical rings connected by straight links.

Referring to FIGS. 8, 10 and 11, each adjacent cylindrical ring 80 may be connected by at least one undulating link 110 or straight link 112. The stent may include only straight links (FIG. 11), may include only undulating links (FIG. 8) or may include both undulating links and straight links (FIG. 10) to connect adjacent cylindrical rings. Both the straight links and the undulating links assist in preventing stent foreshortening. Further, the straight links may provide more stability and rigidity in a localized area, such as at the stent ends, such that it may be desirable to incorporate more straight links between the cylindrical rings at the stent ends, than in the center of the stent. An undulating link may be positioned substantially within the cylindrical plane 90, as defined by the cylindrical outer wall surface 92 and the cylindrical inner wall surface 93.

The fine grain stent 60 of the present invention can be made in many ways. One method of making the stent is to cut a thin-walled tube of fine grain material to remove portions of the tubing in the desired pattern for the stent, leaving relatively untouched the portions of the metallic tubing that are to form the stent. In accordance with the invention, it is preferred to cut the tubing in the desired pattern by means of a machine-controlled laser, as is well known in the art. Other methods of forming the stent of the present invention can be used, such as chemical etching; electric discharge machining; laser cutting a flat sheet and rolling it into a cylinder with a longitudinal weld; and the like, all of which are well known in the art at this time. In addition, the stent and/or its struts may be formed from a wire or elongated fiber constructed from a fine grained material. The cross-section of such struts may be round, rectangular or any other suitable shape for constructing a stent.

Referring now to FIGS. 12 and 13, and by way of example, the present invention may be incorporated into an embolic protection device 120. Such device may include a filter assembly 122 and expandable strut assembly 124. The embolic protection device may further include an elongated tubular member 130, within which may be disposed a guidewire 132 for positioning the device within a corporeal lumen. In accordance with the present invention, the embolic protection device may include a plurality of longitudinal struts 126 and transverse struts 128 that are constructed from a fine grain material according to the present invention. In addition, the filter assembly may be formed from a fine grain material as heretofore described. Similarly, the guidewire may include or be constructed from a fine grain material, and the distal end of the guidewire 134 may also include or be constructed from a fine grain material.

Figure 14:
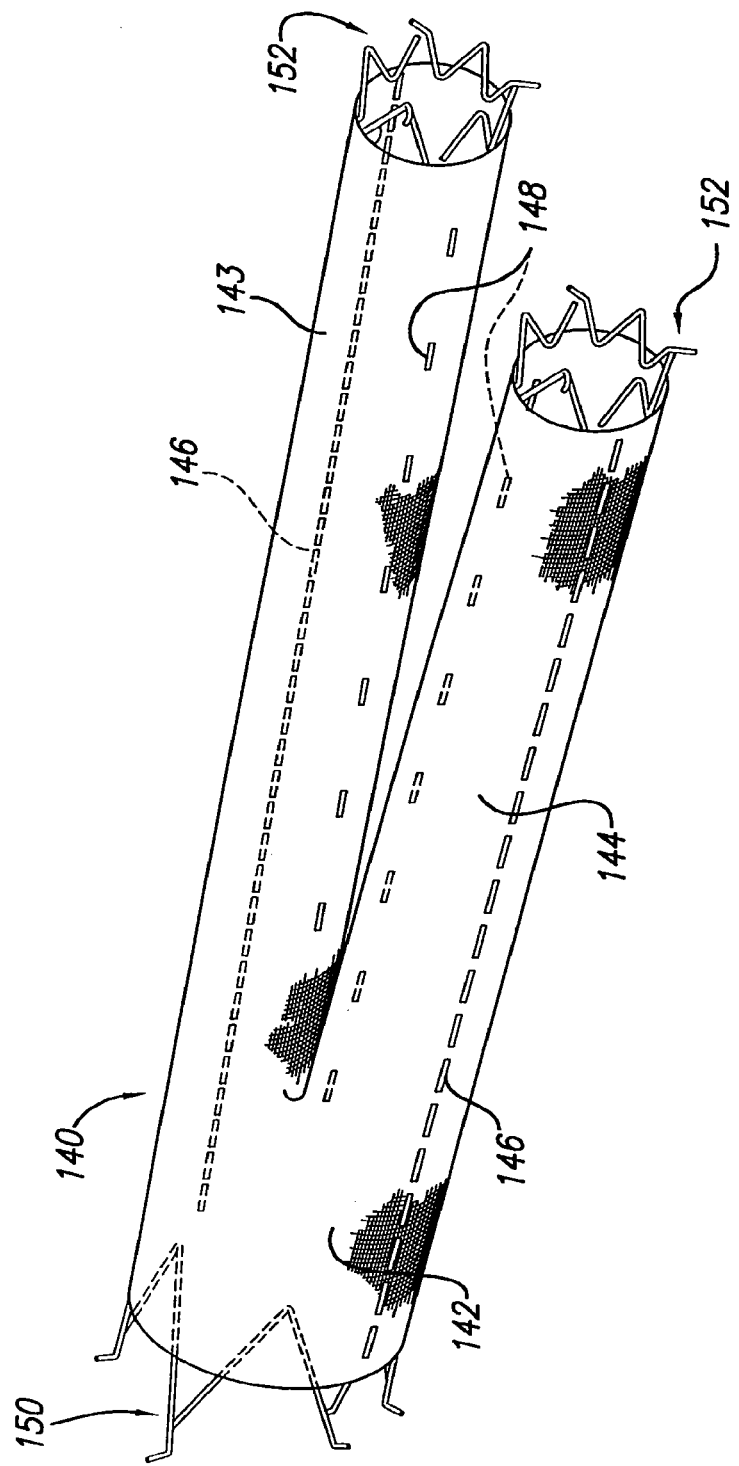
FIG. 14 depicts a perspective view of a graft assembly, including a plurality of fine grain attachment systems of the present invention.

Referring now to FIG. 14, fine grain material of the present invention may be incorporated into a bifurcated graft 140. Likewise, the fine grain material may be incorporated into a tubular graft (not shown). Such a graft includes a DACRON, TEFLON or other suitable flexible material having an upper body 142, a first leg 143 and a second leg 144, wherein the legs are joined to the upper body. Such a configuration forms a "Y" or "pants leg" configuration. A plurality of closely spaced markers 146 formed from a radiopaque fine grain material may be configured on the outside of the first and second legs. Similarly, wider spaced markers 148 may be configured on the inside of the legs of the bifurcated graft (or visa versa). Such markers may be formed from radiopaque fine grain material as heretofore described, which may be sewn, glued or otherwise bonded to the graft.

In many such grafts 140, such as those used for repairing an abdominal aortic aneurysm, the upper body may include a first attachment system 150 positioned proximate to an upper opening of the graft. Tube grafts may contain a like attachment system at the lower opening of the graft. Similarly, bifurcated grafts may include smaller attachment systems 152 positioned at the end of the legs and proximate to the lower openings of the graft. As heretofore described regarding stents (FIGS. 4-11), the attachment system may be made of a variety of fine grain materials in accordance with the present invention. Such stents and attachment systems may be of various configurations, such as, but not limited to, a ring and link design, a zigzag design, a coil design or a tubular mesh design.

While particular forms of the invention have been illustrated and described with regard to certain medical devices, it will also be apparent to those skilled in the art that various modifications can be made without departing from the scope of the invention. More specifically, it should be clear that the present invention is not limited to catheters, tubular type stents, embolic protection devices and endovascular grafts. Likewise, the invention is not limited to any particular method of forming the under lying medical device structure. While certain aspects of the invention have been illustrated and described herein in terms of its use as an intravascular stent, it will be apparent to those skilled in the art that the stent can be used in other body lumens. Further, particular sizes and dimensions, materials used, and the like have been described herein and are provided as examples only. Other modifications and improvements may be made without departing from the scope of the invention. Accordingly, it is not intended that the invention be limited, except as by the appended claims.

What is claimed is:

1. An intravascular prosthesis for use in a body lumen, comprising:
   a plurality of structural members interconnected to form the intravascular prosthesis; and
   each structural member being formed from a material having an average grain size in a range of 1-10 microns selected from the group consisting of a Co—Cr alloy, a Pt—Ir alloy, a Ni—Ti alloy, tantalum, and a tantalum-based alloy.

2. The intravascular prosthesis of claim 1, further comprising at least one straight link attaching a structural member to an adjacent structural member.

3. The intravascular prosthesis of claim 1, further comprising at least one undulating link attaching a structural member to an adjacent structural member.

4. The intravascular prosthesis of claim 1, further comprising at least one undulating link attaching a structural member to an adjacent structural member, and at least one straight link attaching a third a structural member to a fourth structural member.

5. The intravascular prosthesis of claim 1, wherein the intravascular prosthesis is a stent.

6. An intravascular stent for use in a body lumen, comprising:
   a plurality of cylindrical rings interconnected to form the stent, each cylindrical ring having a first delivery diameter and a second expanded diameter; and
   each cylindrical ring being formed from a material having an average grain size in a range of 1-10 microns so as to increase strength and ductility of each cylindrical ring, the material being selected from the group consisting of a Co—Cr alloy, a Pt—Ir alloy, a Ni—Ti alloy, tantalum, and a tantalum-based alloy.

7. The intravascular stent of claim 6, further comprising at least one straight link attaching each cylindrical ring to an adjacent cylindrical ring.

8. The intravascular stent of claim 6, further comprising at least one undulating link attaching each cylindrical ring to an adjacent cylindrical ring.

9. The intravascular stent of claim 6, further comprising at least one undulating link attaching a first cylindrical ring to a first adjacent cylindrical ring, and at least one straight link attaching a second cylindrical ring to a second adjacent cylindrical ring.

10. The intravascular stent of claim 6, wherein each cylindrical ring includes a proximal end, a distal end and a cylindrical wall extending circumferentially between the proximal end and the distal end, and further including an undulating link positioned substantially within the cylindrical wall of a first cylindrical ring so as to attach the first cylindrical ring to an adjacent cylindrical ring.

11. An intravascular stent for use in a body lumen, comprising:
    a plurality of struts interconnected to form a stent, the stent having a first delivery diameter and a second expanded diameter; and
    each strut being formed from a material having an average grain size in a range of 1-10 microns to allow distribution of stresses within some grains in each strut to other grains within the strut, the material being selected from the group consisting of a Co—Cr alloy, a Pt—Ir alloy, a Ni—Ti alloy, tantalum, and a tantalum-based alloy.

12. The intravascular stent of claim 11, wherein the material is a tantalum-based alloy.

13. The intravascular stent of claim 11, wherein the material is a Co—Cr alloy.

14. An intravascular prosthesis for use in a body lumen, comprising:
    a plurality of structural members interconnected to form the intravascular prosthesis; and
    each structural member being formed from a material having an average grain size in a range of 1-10 microns to allow distribution of stresses within some grains in each structural member to other grains within the structural member, the material being selected from the group consisting of a cobalt alloy, a Pt—Ir alloy, and a tantalum-based alloy.

15. The intravascular stent of claim 14, wherein the at least one material is a cobalt alloy.

16. The intravascular stent of claim 14, wherein the at least one material is a Pt—Ir alloy.

17. The intravascular stent of claim 14, wherein the at least one material is a tantalum-based alloy.

\* \* \* \* \*